US006685666B1

(12) United States Patent
Fontenot

(10) Patent No.: US 6,685,666 B1
(45) Date of Patent: Feb. 3, 2004

(54) CATHETERS FOR BREAST SURGERY

(76) Inventor: Mark G. Fontenot, 220 Marilyn Dr., Lafayette, LA (US) 70503

( * ) Notice: Subject to any disclaimer, the term of this patent is extended or adjusted under 35 U.S.C. 154(b) by 0 days.

(21) Appl. No.: 09/711,066

(22) Filed: Nov. 9, 2000

Related U.S. Application Data
(60) Provisional application No. 60/165,311, filed on Nov. 12, 1999.

(51) Int. Cl.⁷ .......................... A61M 1/00; A61M 31/00
(52) U.S. Cl. .................. 604/27; 604/500; 604/508; 604/264; 600/478; 600/473
(58) Field of Search ................. 604/500, 506, 604/509, 510, 511, 513, 517, 93.01, 103.08, 104, 105, 106, 107, 108, 109; 600/473, 476

(56) References Cited

U.S. PATENT DOCUMENTS

| 4,813,930 | A | * | 3/1989 | Elliott ........................ 600/585 |
| 5,423,321 | A | | 6/1995 | Fontenot |
| 5,540,659 | A | * | 7/1996 | Teirstein ..................... 604/104 |
| 5,782,771 | A | | 7/1998 | Hussman |
| 5,879,306 | A | * | 3/1999 | Fontenot et al. ............ 600/473 |
| 6,159,196 | A | * | 12/2000 | Ruiz .......................... 604/500 |
| 6,178,346 | B1 | * | 1/2001 | Amundson et al. ......... 600/473 |
| 6,296,608 | B1 | * | 10/2001 | Daniels et al. .............. 600/478 |

* cited by examiner

Primary Examiner—Manuel Mendez
Assistant Examiner—Matthew F DeSanto
(74) Attorney, Agent, or Firm—Townsend and Townsend and Crew LLP

(57) ABSTRACT

Methods and systems for accessing target sites in breast and other tissues comprising catheters having hooks or other anchoring means at their distal ends. The positions of the catheters and tissue are determined using a light source, optionally using both infrared and visible light sources. Once accessed, drugs may be delivered through the catheter, or the catheter may be used to facilitate surgical intervention.

7 Claims, 18 Drawing Sheets

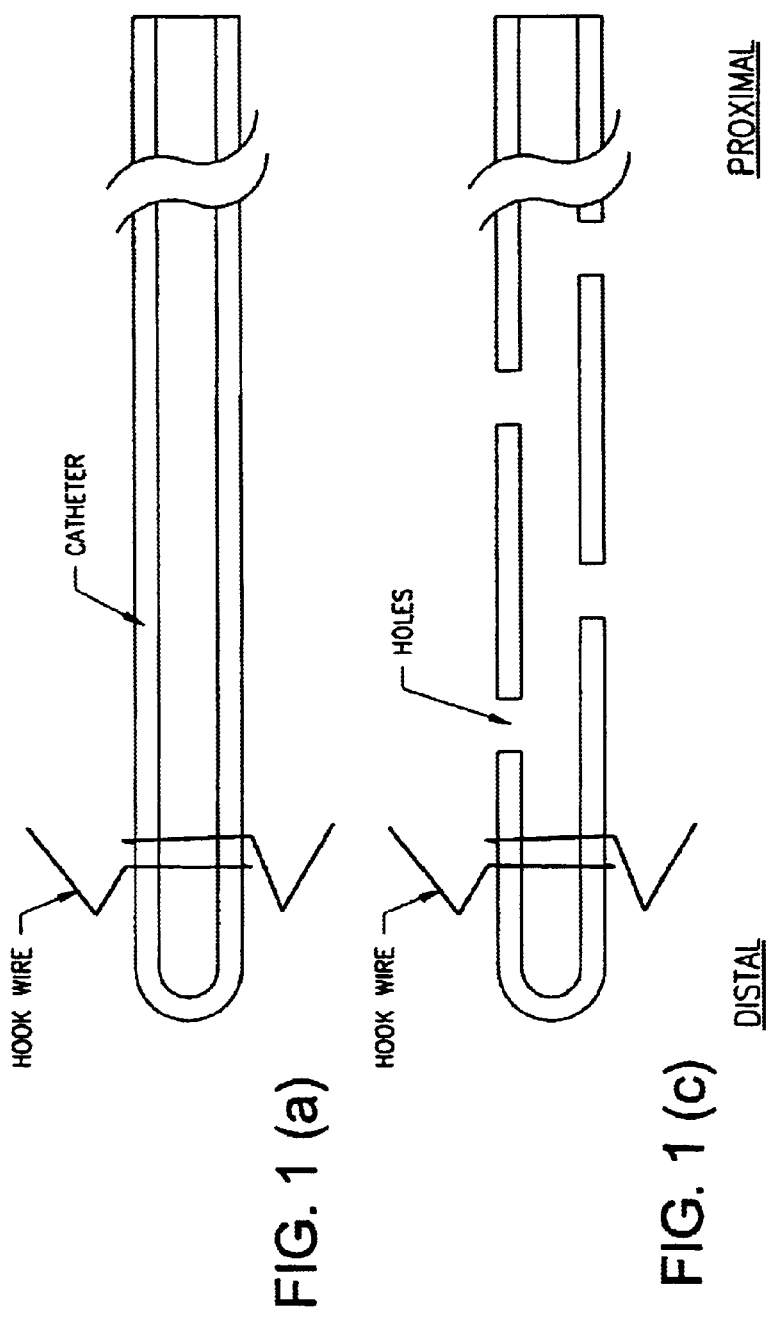

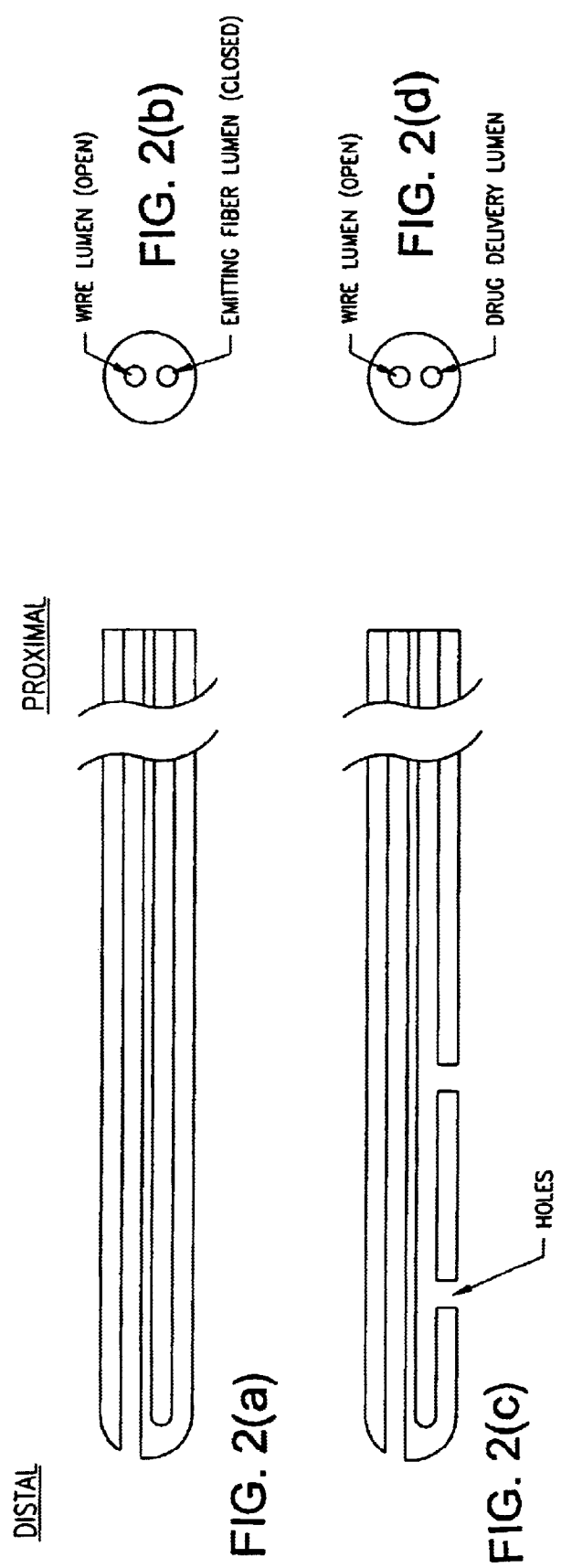

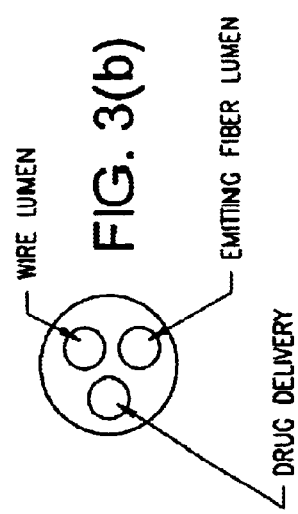
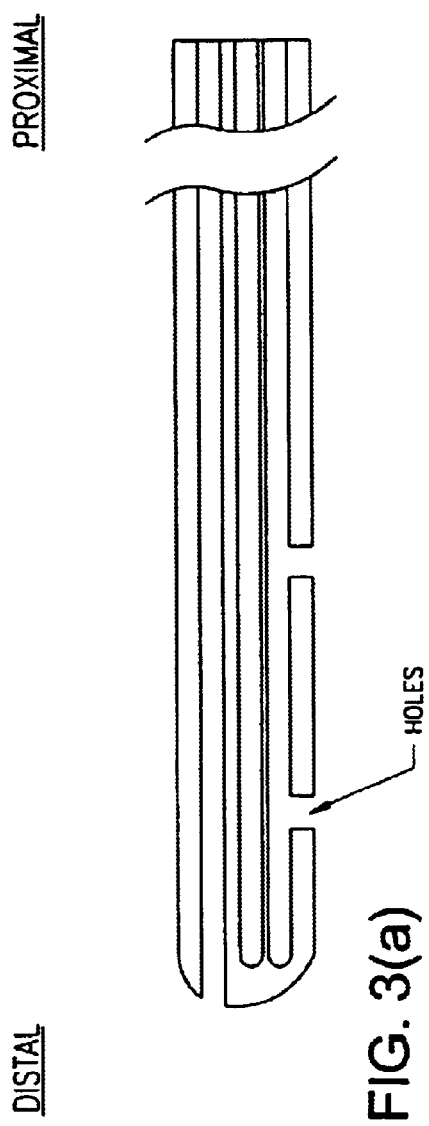

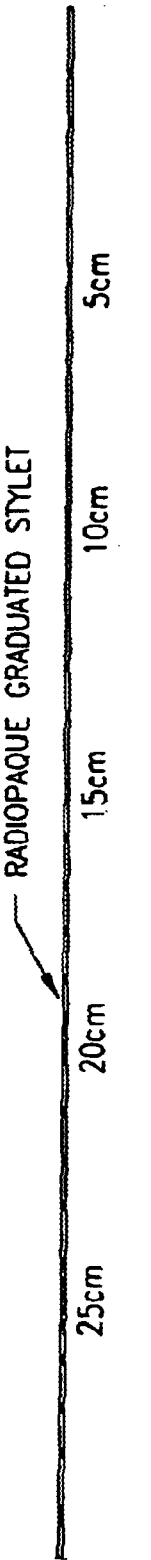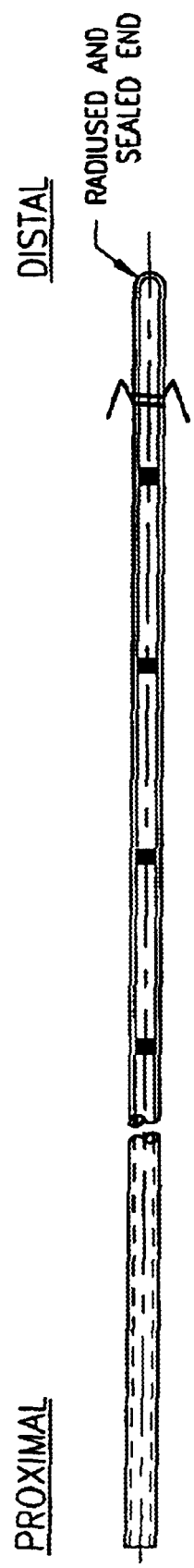
FIG. 4(a)
FIG. 4(b)

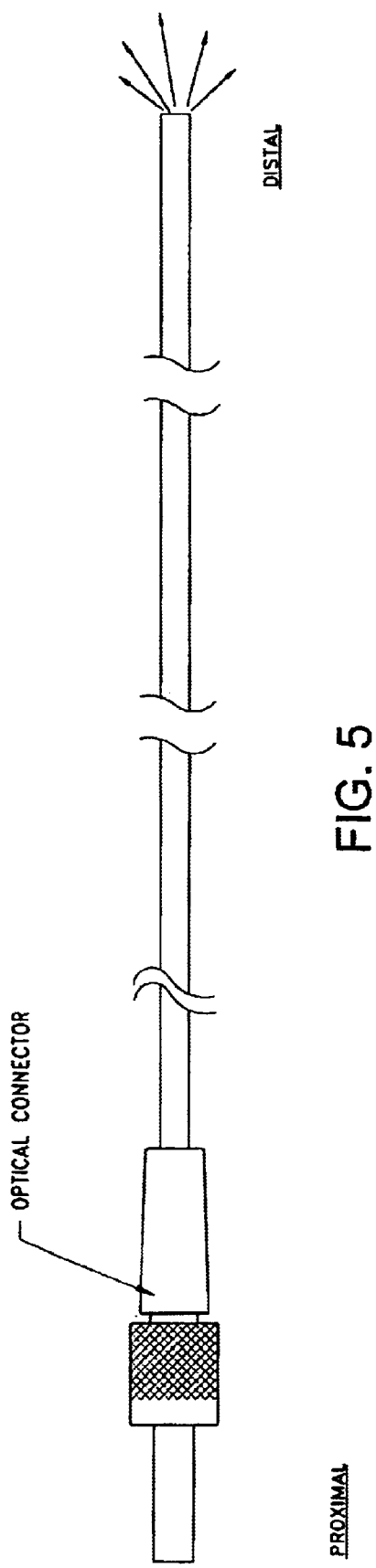

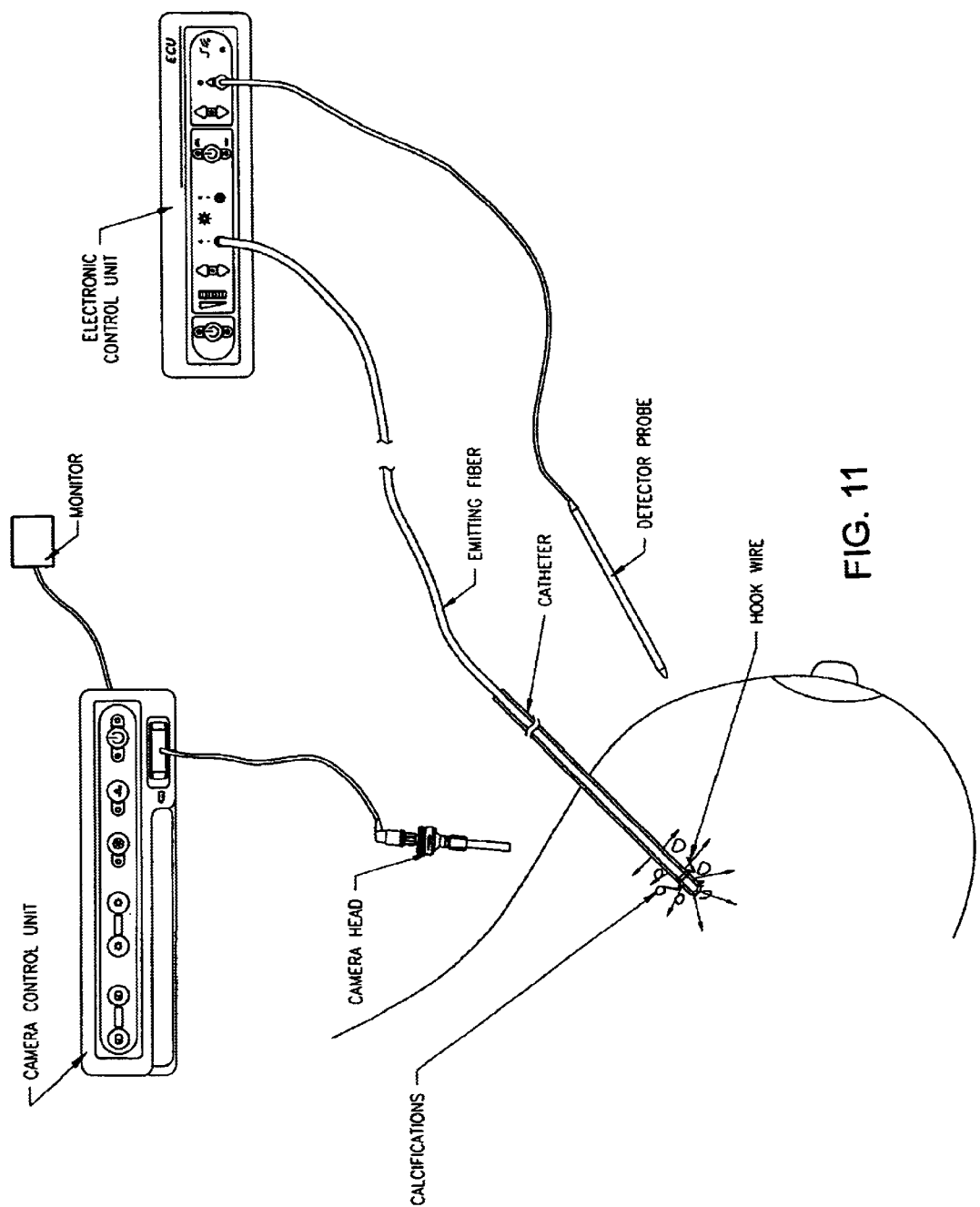

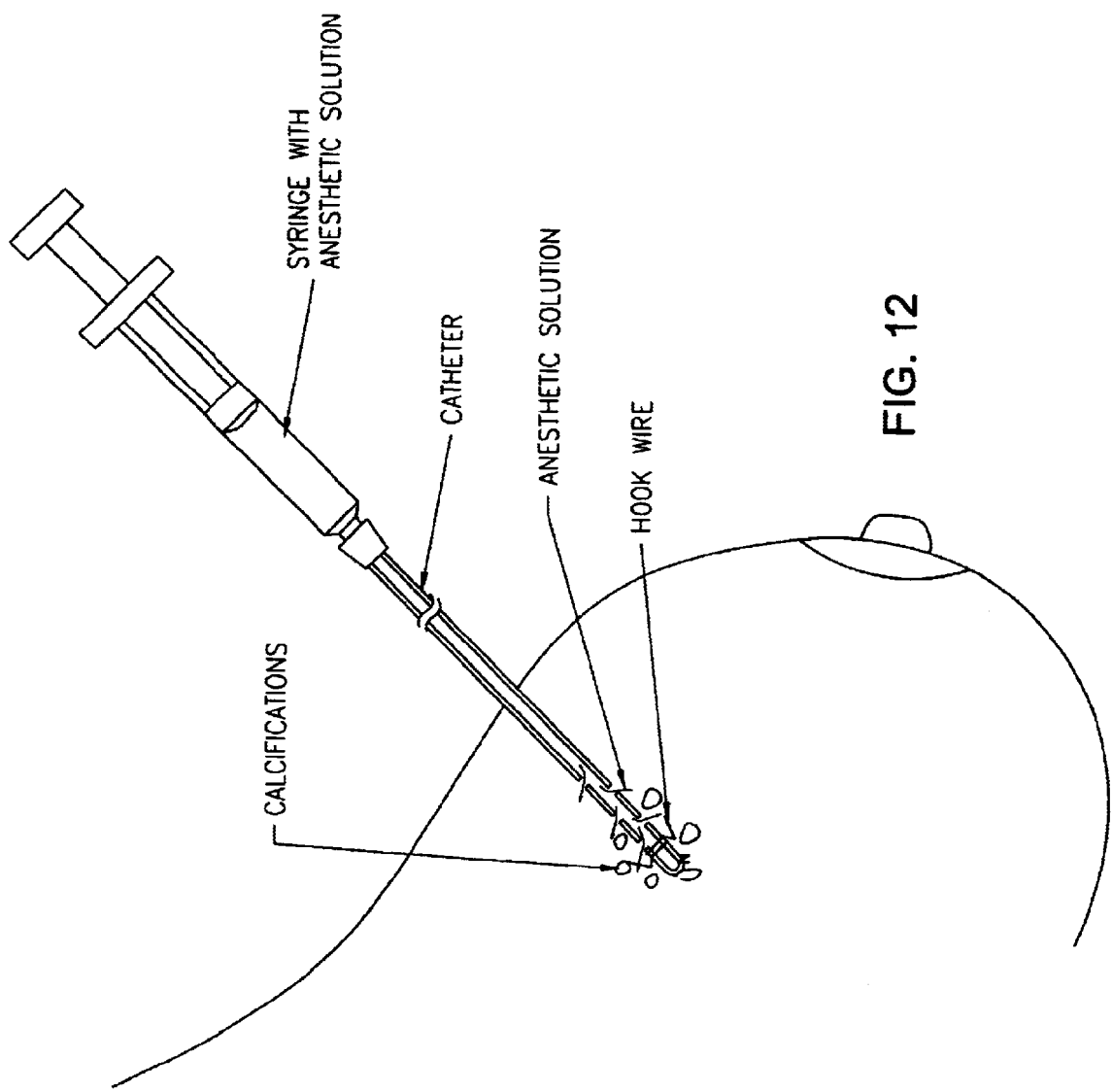

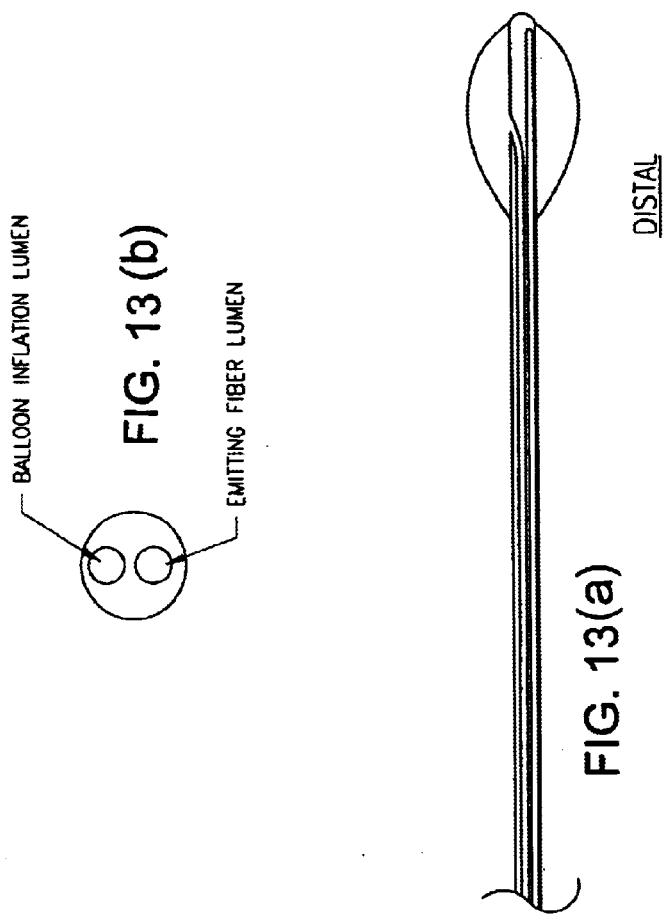
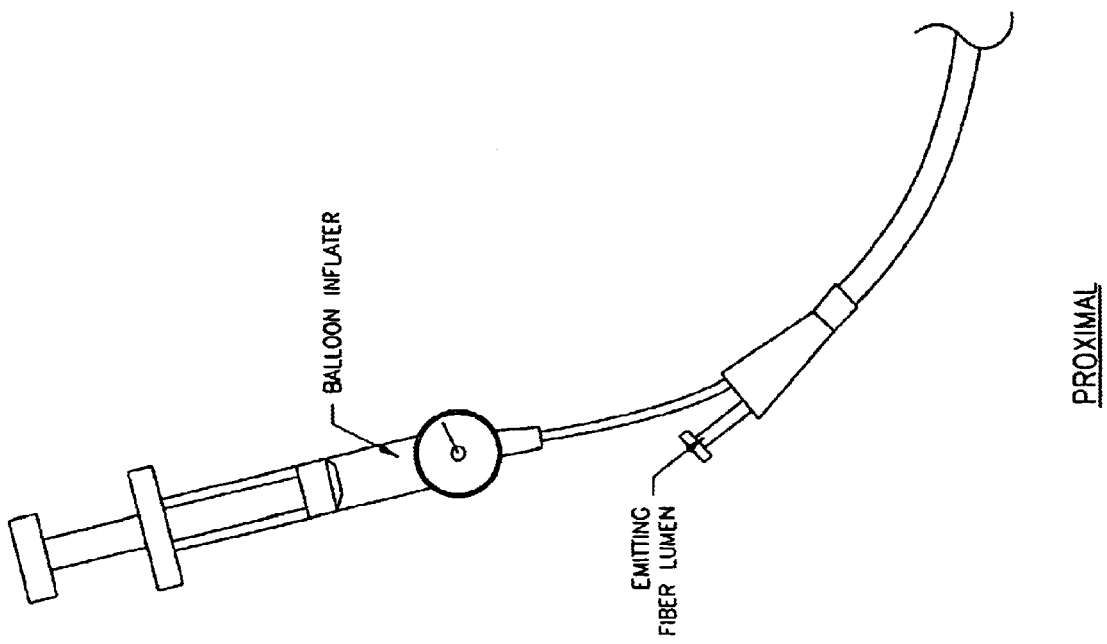
FIG. 13(b)
FIG. 13(a)

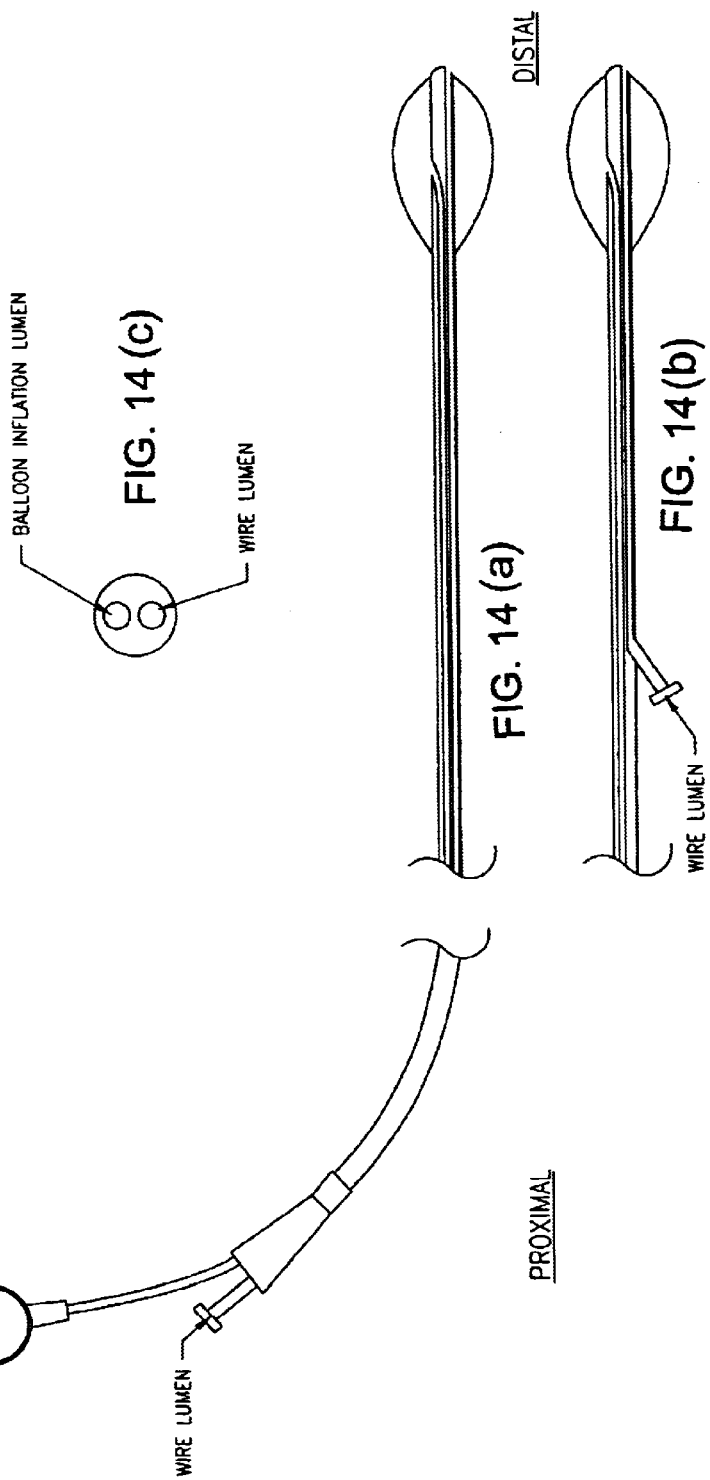

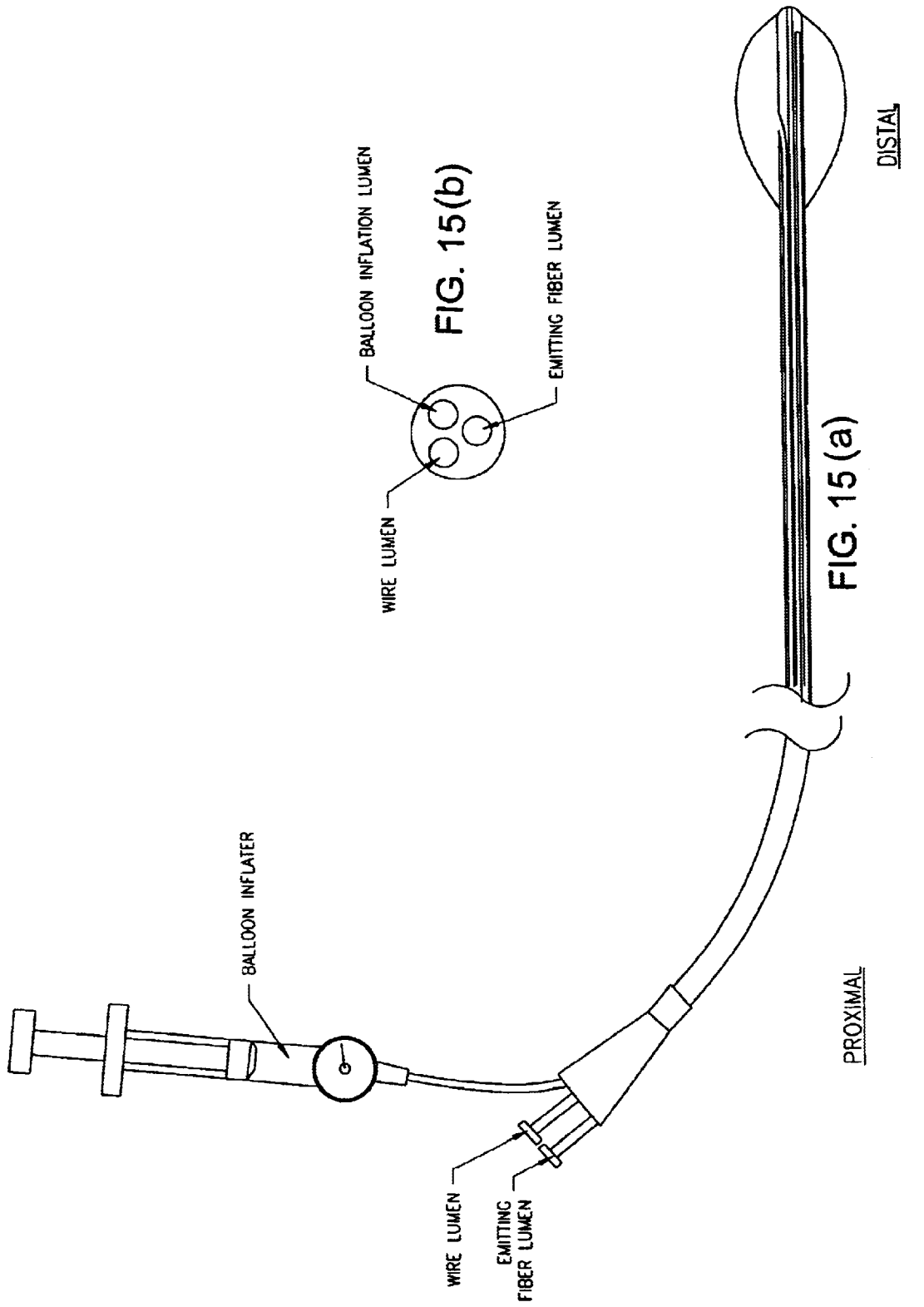

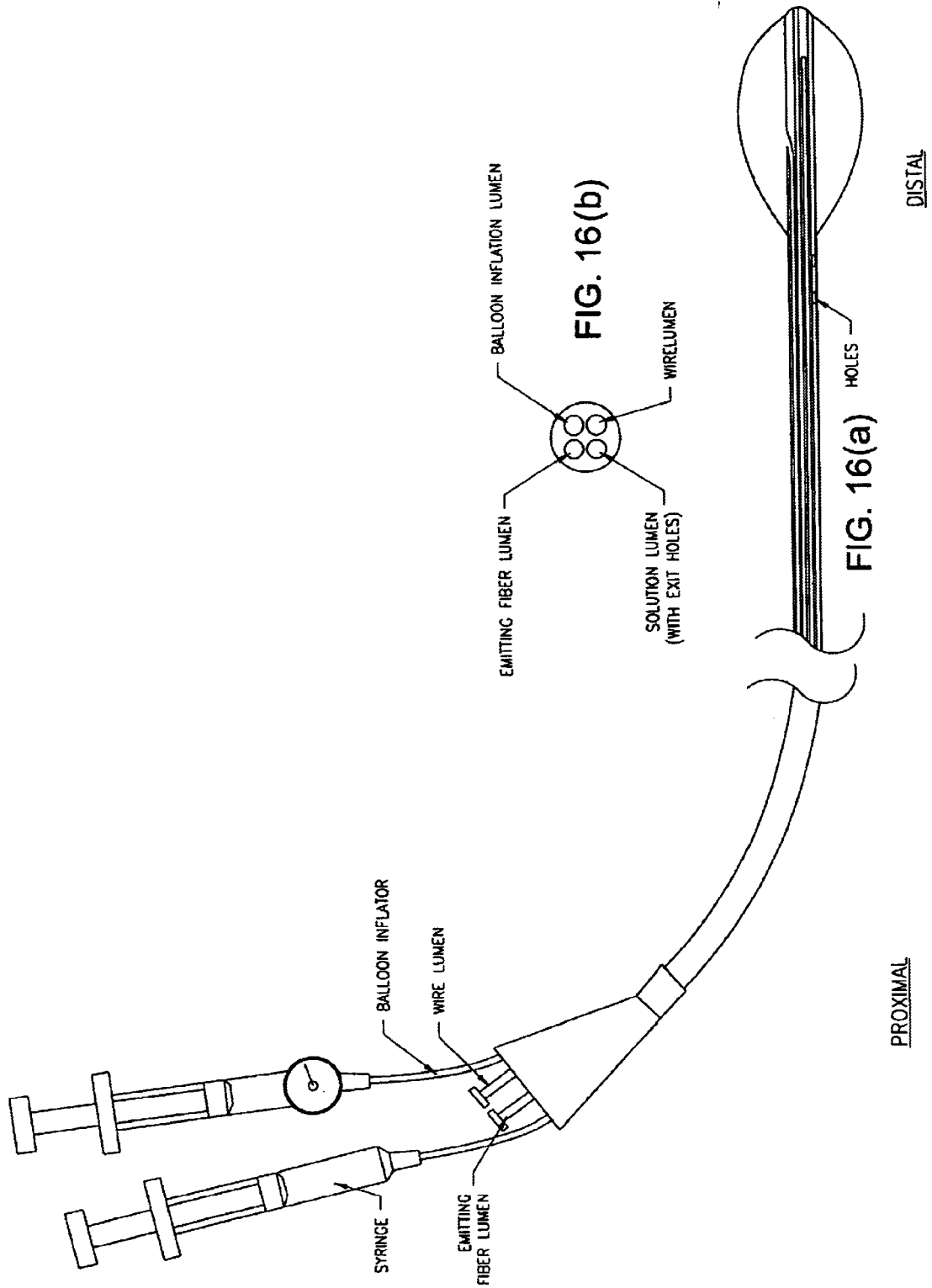

CATHETERS FOR BREAST SURGERY

This application claims the benefit of Provisional application Ser. No. 60/165,311 filed Nov. 12, 1999.

BACKGROUND OF THE INVENTION

1. Field of the Invention

The present invention relates to invasive methods and devices which position and anchor single or multiple lumen catheters proximate to breast lesions under radiographic guidance in order to provide a conduit or conduits for reversible placement of devices such as an optical fiber or allow the delivery of medicament or drug solutions such as anesthetic to sites in breast tissue along the length of the catheter.

2. Background of the Invention

There is an abundance of published literature surrounding wire needle localization (WNL) and its use in breast biopsy. Specifically, WNL is a surgical technique frequently invoked by surgeons to biopsy lesions in the breast discovered as a result of mammography or other breast screening methods. Patients undergoing WNL are placed on a radiographic table usually located in the radiology suite. The breast is placed between two compression plates, arranged moveably in relation to one another, for fixing the breast there between. The compression plates have holes which permit the introduction of a biopsy needle under radiographic guidance into the breast and proximate to the breast lesion to be biopsied. Once the needle is placed in the desired position in the breast, a thin, stiff wire with a distal retaining hook is inserted through the lumen of the needle. As the wire emerges from the distal aspect of the needle, the distal hook of the wire engages the breast tissue proximate to the breast lesion. The needle is withdrawn leaving the hook wire proximate to the lesion. The position of the wire relative to the lesion is verified radiographically. Radiographic views of the wire in the breast are taken and brought to the operating room so as to allow the surgeon to plan the surgical biopsy procedure.

The patient is transferred to the operating room. After physically examining the breast and placement of the wire in the breast as well as the radiographs of the wire placement, the surgeon plans the surgical approach for the removal of the desired breast tissue specimen. The wire serves as a marker which can be palpated by the surgeon during surgery. Using a typical syringe and needle, local anesthetic is administered in and around the proposed surgical area. An incision is made and the surgeon dissects around the wire. During the dissection, the surgeon continuously palpates the location of the wire in order to orient the dissection and determine that amount of tissue to be harvested or biopsied. The surgical objective of the biopsy is to remove an adequate tissue sample such that the wire and the lesion are at the center of the sample surrounded by an adequate margin thickness of normal breast tissue.

In U.S. Pat. No. 5,782,771 entitled "Dual, Fused, and Grooved Optical Localization Fibers," Hussman discloses the use of an optical fiber or bundle of optical fibers with a hook fixed to the distal aspect of the optical fiber or fiber bundle. The optical fiber-hook assembly can be passed through the lumen of a needle. As the optical fiber-hook assembly exits the needle and enters the breast tissue, the hook engages the tissue thus anchoring the optical fiber-hook assembly within the breast tissue. The other end of the optic fiber or fiber bundle can be connected to a light source. Light traverses the length of the optical fiber and transillu-minates breast tissue and exits at the distal end of the optical fiber. The optical fiber enables the surgeon to identify the tip of the optical fiber by the light which originates from a light source such as a 15 mW 635 nm red laser diode. The tip of the optical fiber can be detected with the eye (since the eye is sensitive to 635 nm) if the tissue overlying permits ample light transmission for the eye to detect. If the tip of the optical fiber is buried deep in breast tissue and not visible to the eye, then a probe fabricated from optical fiber is invasively inserted into the breast. When the probe tip is maneuvered to a location near the fiber tip emitting light, the probe tip captures lights departing from the fiber tip. Light is transmitted along the length of the probe and exits the probe and incident upon the eye. The eye may detect light emanating from the distal end of the prove if sufficient light is emitted by the optical tip and transmitted to the eye via the probe. The operating room lights may have to be dimmed in order to improve performance of the Hussman technique.

Optically, all biological tissues are considered composite structures consisting of a scattering medium imbibed with various molecular components which collectively absorb or scatter light at specific wavelengths, i.e. the body is a spectral filter that selectively scatters or absorbs electromagnetic energy as a function of wavelength. In the range of 200 nm to 1,500 nm, the amount of light absorbed or scattered by different molecules is dependent on the chemical and physical properties of the molecule. In the visible part of the electromagnetic spectrum (400 nm to 700 nm), absorption due to tissues and tissue components coupled with light loss caused by scattering results in varying transmissivity of visible light through tissue. In the infrared spectrum above 1,300 nm, water present in tissue acts as an effective absorber of infrared, again limiting the transmission of infrared wavelengths longer than 1,300 nm. However, in the infrared range of 700 to 1,300 nm, infrared light has a relatively high transmissivity compared to visible light. This window of transmissivity (a measure of light transmission) is due to the lack of molecular components that strongly absorb infrared between 700 nm and 1,300 nm.

Fontenot, in U.S. Pat. No. 5,423,321 entitled "Detection of Anatomic Passages Using Infrared Emitting Fiber," describes a method and devices which take advantage of the body's inherently high light transmissivity in the near infrared range (700 nm to 1,300 nm). U.S. Pat. No. 5,423,321 describes intraluminal infrared transillumination of natural passages in the body such as the ureter which is a duct connecting the kidney to the bladder. A ureteral catheter enters the body through natural passages, specifically the vaginal orifice first, then the lumen of the urethra, bladder, and into the lumen of the ureter with the aid of a cystoscope. A plastic fiberoptic light guide is fitted into the lumen of the ureteral catheter and coupled to an infrared laser diode. Infrared laser light transilluminating the ureter and overlying tissues is detected with either a video system sensitive to near infrared or a detector probe coupled to a photodetector that is also sensitive to infrared.

As previously discussed, Hussman, in U.S. Pat. No. 5,782,771, describes a novel method and device for anchoring an optical fiber in breast tissue. However, fixing anchoring devices to the tip of optical fibers can weaken or embrittle the fibers causing the fiber to break in tissue while residing in the body. Also, in U.S. Pat. No. 5,782,771, Hussman uses visible light to transilluminate tissue overlying the tip of the optical fiber. Visible light is strongly attenuated by tissues. Thus, to detect the fiber tip emitting visible light in breast tissue and overlying skin, Hussman invasively introduces a probe consisting of a fiber or fiber bundle. The probe is directed towards the fiber tip which is emitting light. Subsequently, light captured by the distal end of the fiberoptic probe travels the length of the probe and exits the opposite end. The human eye may detect the emitted light from the probe if the room lights are dimmed and adequate light is transmitted from the tip of the optical fiber emitting light to the eye through the probe. Hussman does not discuss or present methods or devices that would allow the following: (1) the use of non-invasive methods and devices to detect the fiber tip such as the use of infrared emission-detection techniques, (2) the use of a conduit or catheter that could be fixed or anchor in tissue which would facilitate the reversible placement of a fiberoptic light guide into the lumen of a catheter.

Also, as previously discussed, Fontenot in U.S. Pat. No. 5,423,321, uses a non-anchoring catheter that enters the body through natural passages. For example, to enter the ureter in a female, a cystoscope is introduced into the vagina and into the lumen of the urethra, bladder, and into the lumen of the ureter. The ureteral catheter is then placed in the ureter and the cystoscope retracted. Fontenot transilluminates the natural passage using an emitting fiber and an infrared light source. Detection of the passage is facilitated with a detector probe or video system, both of which are sensitive to infrared light since the human eye cannot detect near infrared. Fontenot does not discuss or present methods or devices that would allow the following: (1) placement of a catheter that is fixed or anchored to the tissue using devices such as a hook wire at the distal aspect of the catheter, (2) placement of the catheter under radiographic guidance, (3) an over the wire method used to guide the catheter to a desired location, and (4) the invasive placement of catheter into tissue or an organ that is not through a natural passage.

OBJECTS OF THE INVENTION

It is an object of this invention to invasively insert a catheter under radiographic guidance into the breast and proximate to a breast lesion that forms a conduit for reversible placement of devices such as an emitting fiber or allow medicament or drug solutions such as anesthetic solutions to be delivered to sites in breast tissue along the length of the catheter.

It is another object of the present invention to invasively insert a catheter using an over the wire method, such wire that has been previously placed under radiographic guidance, thus forming a conduit for the reversible placement of devices such as an emitting fiber or allow medicament or drug solutions such as anesthetic solutions to be deliver to sites in breast tissue along the length of the catheter.

In accordance with another embodiment, a catheter with a wire hook or balloon can be fabricated or attached to the distal aspect of the catheter which functions to retain or anchor the catheter in breast tissue.

In yet another embodiment, an emission-detection is used to detect the tip of the catheter in breast tissue or track the course of the catheter in breast tissue.

SUMMARY OF THE INVENTION

The present invention relates to invasive placement of single or multi-lumen catheters in the breast tissue under radiographic guidance for the purposes of providing at least: (1) a landmark within the breast and adjacent to a target breast lesion, (2) a conduit for devices such as an optical fiber, (3) a conduit for the delivery of solutions containing medicaments or drugs to site in the breast along the length of the catheter, and (4) a means for anchoring such catheter in breast tissue. More specifically, the present invention consists of a catheter that can be fixed or anchored in breast tissue and provide a conduit for reversibly placing devices such as fiberoptic light guide into a desired position in the lumen of the catheter. The catheter has a means for anchoring the distal end of the catheter and such catheter can be placed proximate to a breast lesion under radiographic guidance. Exemplary means for anchoring catheters include mechanical devices, such as a hook wire or, an expansible anchor (e.g. a mallecott structure), an inflatable balloon formed at the distal end of the catheter. In one embodiment, an over the wire method is used to place a catheter proximate to a breast lesion. To aid in breast dissection and orientation, a visible or infrared light emission-detection scheme is used to detect the tip of the catheter or the course of the catheter as it tracks through breast tissue and exits the breast is also embodied in the invention.

BRIEF DESCRIPTION OF THE DRAWINGS

FIG. 1 Side and cross sectional views of a single lumen, optically transparent catheter with a hook wire fixed to the distal tip. FIG. 1(a) shows a side view of a single lumen, transparent catheter without lateral holes. FIG. 1(c) shows a catheter with staggered lateral holes placed in the distal portion of the catheter. FIGS. 1(b) and 1(d) show the cross section view of the single lumen catheter.

FIG. 2 Side and cross sectional views of an over the wire, transparent catheter. FIG. 2(a) shows a side view of the over the wire catheter with the top lumen open at both ends. The top lumen (FIGS. 2(a) and 2(c)) serves as a guide when the proximal end of a wire previously placed in the breast under radiographic guide is fitted into the distal entrance of the top lumen and the catheter advanced over the wire to the desired position. The distal end of the lower lumen in FIG. 2(a) is closed. An emitting fiber, radiopaque stylet, or other device can be fitted into the proximal entrance of the lower lumen and advanced to a desired position. FIG. 2(c) shows a side view of the over the wire catheter with the holes in the lower lumen. The distal end of the lower lumen in FIG. 2(c) can be open or closed. In FIG. 2(c), the catheter is shown closed with holes placed in the distal aspect of the catheter. In FIG. 2(c), the lower lumen provides a conduit for the delivery of drug solutions such as anesthetic solutions to a desired site or sites in the breast along the length of the catheter. In addition, the lower lumen in FIG. 2(c) can also house an emitting fiber, radiopaque stylet or other device. Cross sectional views in FIGS. 2(b) and 2(d) show one possible configuration of the dual lumen over the wire catheter.

FIG. 3 Side and cross sectional views of a three lumen over the wire catheter. In FIG. 3(a), the top lumen is open at the proximal and distal ends and serves as a guide when the proximal end of a wire previously placed in the breast under radiographic guide is fitted into the distal entrance of the top lumen and the catheter advanced over the wire to a desired position. The second lumen is closed at the distal end and can house an emitting fiber, radiopaque stylet, or other device. The third lumen can be open or close at the distal with holes placed along the distal portion of the catheter. The third lumen serves as a conduit for the delivery of solutions such as anesthetic solutions at a desired site in the breast. FIG. 3(b) shows a cross sectional view of the 3 lumen catheter.

FIG. 4 Side view of a single lumen hook wire catheter with a graduated radiopaque stylet. The graduated radiopaque stylet (FIG. 4(a)) can be fitted into the lumen of the hook wire catheter in FIG. 4(b) or any of the catheters discussed in this disclosure. The graduated radiopaque stylet gives the surgeon and/or the radiologist an indication as the approximate location of the breast lesion relative to the catheter and/or skin when fitted into the lumen of a catheter that is proximate to the breast lesion.

FIG. 5 Side view of a fiberoptic light guide that is end emitting.

FIG. 11 Schematic showing the fiberoptic light guide reversibly coupled to the electronic control unit. Laser light is launched into the fiber and emitted radially from the wall and end of the fiberoptic light guide. Near infrared laser light, not visible to the eye, can be detected with a video system that is sensitive to visible and near infrared light (visible aspect). The infrared laser diode can be modulated, such that the breast tissue either appears on the video monitor to be "blinking" or is transilluminated continuously. The surgeon also has the option to use the detector probe coupled to the detection panel of the ECU for audible detection of the infrared transilluminated breast tissue (audible aspect). The detector probe is maneuvered until an audible sound is broadcast from the ECU, which indicates detection of the infrared transilluminated breast tissue.

FIG. 12 Schematic of a single lumen hook wire catheter reversibly coupled to a syringe delivering anesthetic solution to an area adjacent to the lesion and along the length of the catheter. The staggered holes in the distal aspect of the catheter allow solution to delivered to the breast tissue along the length of the catheter.

FIG. 13 Side and cross sectional view of the dual lumen balloon catheter. FIG. 13(a) shows an inflation syringe reversibly coupled to the balloon inflation lumen at the proximal end of the balloon catheter. The balloon at the distal end of the catheter is shown inflated. The distal end of the balloon lumen is continuous with the balloon and serves as a conduit for fluid discharged from the balloon inflater to the lumen of the balloon via the balloon inflater. Fluid discharged from the balloon inflater enters the balloon causing the balloon to be inflated. The balloon can also be deflated by retracting the plunger of the inflater. Once deflated, the balloon catheter can be removed from the breast. The second lumen is sealed at the distal end and can house an emitting fiber, radiopaque stylet, or other device. FIG. 13(b) shows a cross section of the dual lumen balloon catheter.

FIG. 14 Side and cross sectional view of the over the wire balloon catheter. FIG. 14(a) shows an inflation syringe reversibly coupled to the balloon inflation lumen at the proximal end of the balloon catheter. The balloon at the distal end if shown inflated. The distal end of the balloon lumen is continuous with the balloon and serves as a conduit for fluid discharged from the balloon inflater to the lumen of the balloon via the balloon inflation lumen. Fluid discharged from the balloon inflater enters the balloon lumen causing the balloon to be inflated. The balloon can also be deflated by retracting the plunger of the inflater. Once deflated, the balloon catheter can be removed from the breast. The wire lumen is open at the proximal and distal end. In FIGS. 14(a), 14(b), and 14(c), the wire lumen serves as a guide for the balloon catheter as a wire previously placed in the breast under radiographic guide is fitted into the distal entrance of the lumen and the catheter advanced over the wire to the desired position. FIG. 14(a) shows the wire exit port at the proximal aspect of the catheter. FIG. 14(b), show a wire exit port that allows the wire to exit along the length of the catheter. FIG. 14(c) shows a cross section of the dual lumen balloon catheter.

FIG. 15 Side and cross sectional view of an over the wire emitting fiber balloon catheter. The over the wire emitting fiber balloon catheter has three lumens, the balloon inflation lumen, wire lumen, and an emitting fiber lumen.

FIG. 16 Side and cross sectional view showing the over the wire emitting drug delivery balloon catheter. The over the wire emitting drug delivery balloon catheter has four lumens including a balloon inflation lumen, wire lumen, drug delivery lumen, and an emitting fiber lumen.

DESCRIPTION OF THE SPECIFIC EMBODIMENTS

Hook Wire Catheter

Figure 7:
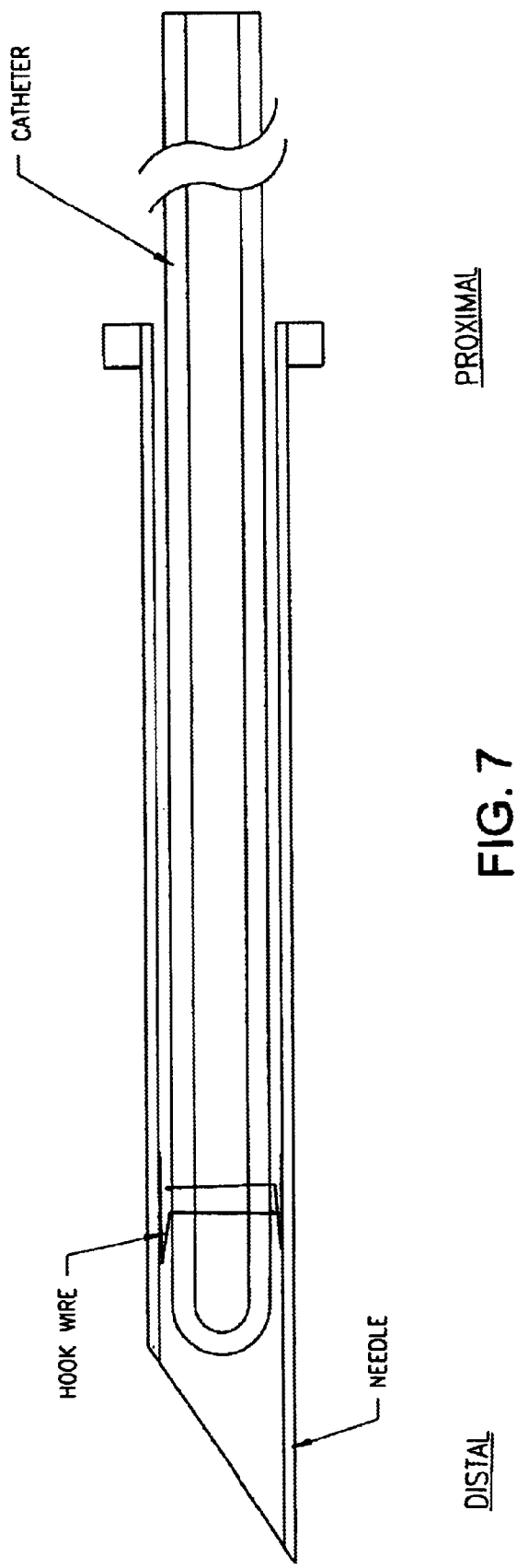
FIG. 7 Side view of a needle-hook wire catheter assembly. A single lumen catheter with a hook wire is reversibly fitted into the lumen of a needle.

The hook wire catheter depicted in FIG. 1(a) is an optically transparent single lumen catheter with a hook wire fixed to the distal aspect. The outside diameter (O.D.) of the hook wire catheter can range from 1 French (Fr; 3Fr=1 mm) and larger. The catheter is fabricated from biocompatible polymers and is flexible. Radiopaque markers can be placed along the length of the catheter to radiographically determine the depth of placement. The hook wire can be fabricated from a biocompatible material such as 316L stainless steel. The hook wire catheter can be reversibly placed in the lumen of a needle (FIG. 7). The distal aspect of the hook wire catheter is introduced into the lumen of needle from the proximal aspect of the needle and advanced as shown in FIG. 7. The arms of the hook wire are compressed against wall of the needle and remain in the lumen of the needle until positioned proximate to the breast lesion.

Figure 8:
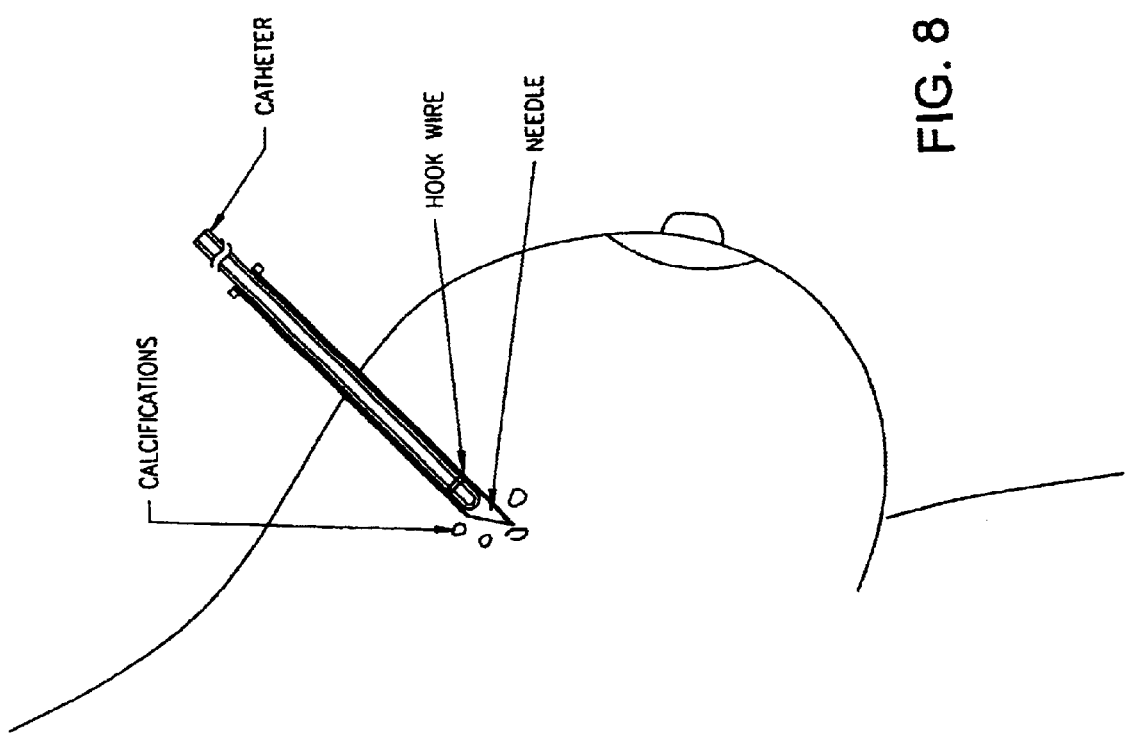
FIG. 8 Side view of a single lumen catheter with a hook wire reversibly fitted into the lumen of a needle that is placed proximate to a breast lesion under radiographic guidance.
Figure 9:
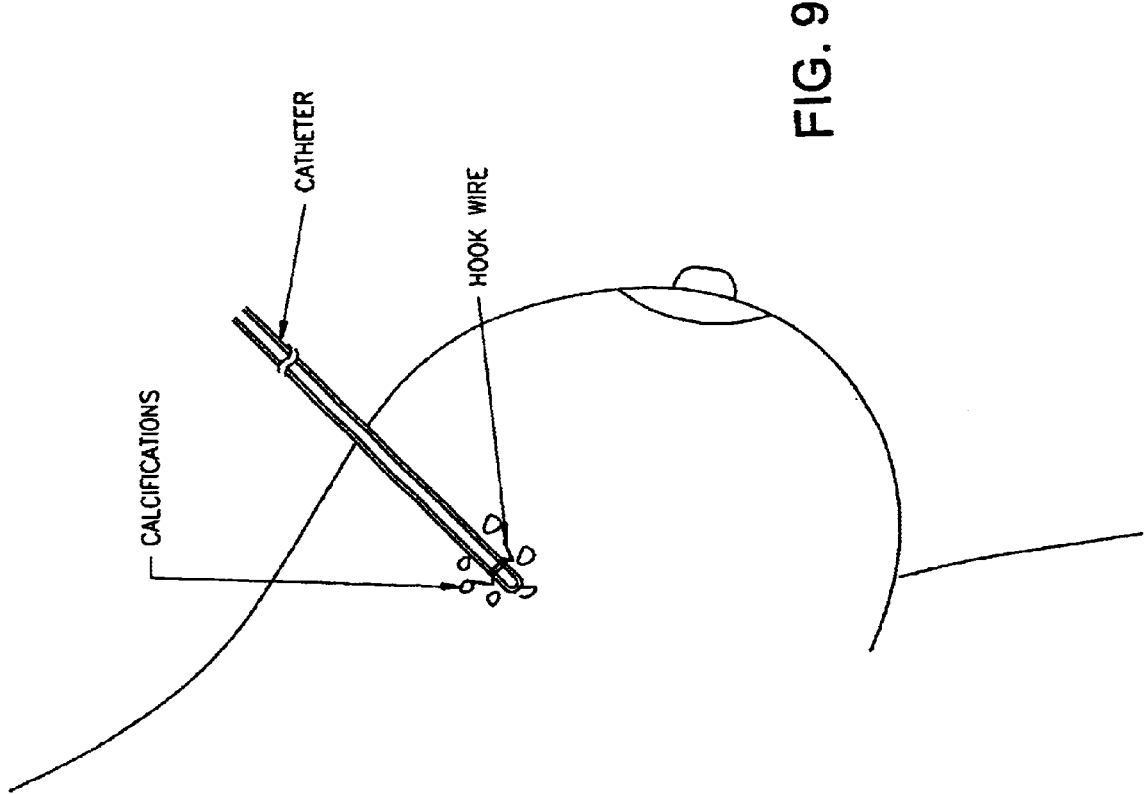
FIG. 9 Schematic of a single lumen hook wire catheter engaged in breast tissue proximate to a breast lesion.

To place the hook wire catheter proximate to the breast lesion, the breast is placed between two moveable compression plates and compressed to the desired amount. The compression plates have holes which permit the introduction of the needle-hook wire catheter assembly (FIG. 7) under radiographic guidance into the breast and proximate to the breast lesion (FIG. 8). Once the needle-hook wire catheter assembly is placed in the desired position in the breast, the hook wire catheter is advanced and emerges from the distal end of the needle. The hook engages the breast and becomes anchored in the breast (FIG. 9). A radiograph is taken to ensure proper placement of the hook wire catheter (FIG. 9). The hook wire is fabricated from metal such as stainless steel and appears as a radiopaque image on a radiograph. The depth of the hook wire catheter relative to the skin surface and the distal aspect of the catheter can be determined by introducing the graduated radiopaque stylet (FIG.

4) into the lumen of the hook wire catheter. The relative position of the graduated radiopaque stylet to the distal end of the hook wire catheter can be determined radiographically or by recording the depth from the graduated marking on the stylet.

Figure 10:
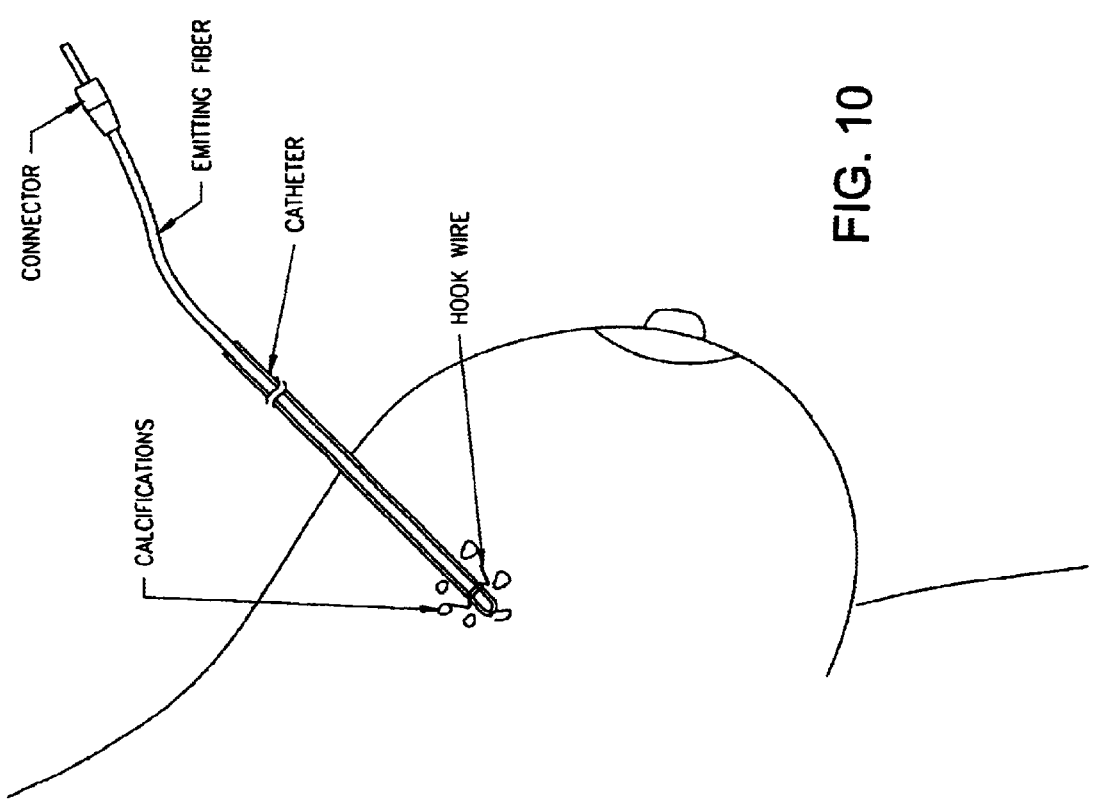
FIG. 10 Schematic of an end and side emitting fiberoptic light guide reversibly fitted into the lumen of a single lumen hook wire catheter placed proximate to a breast lesion.

Once the patient is positioned on the operating room table, the fiberoptic light guide or emitting fiber is reversibly fitted into the lumen of hook wire catheter (FIG. 10). Referring to FIG. 11, the optical connector of the emitting is reversibly coupled to the laser diode housed in the electronic control unit (ECU). The emitting fiber shown in FIG. 10 is end and side emitting (FIG. 5) fiberoptic light guide. FIG. 4 shows an end emitting fiberoptic light guide.

The ECU in FIG. 11 consist of two electronic modules, a laser light source and light sensor, all housed in one unit (FIG. 11). The ECU is DC powered. The ECU houses two variable power laser diodes, one red laser diode (600 nm to 700 nm) and one infrared laser diode (701 nm to 1,100 nm); and has a photodetector and circuitry that is tuned to the modulation frequency and wavelength of the laser diodes. The emitting fiber residing in the catheter is reversibly coupled to a desired laser diode of the ECU. Electronic detection of the emitting segment of the emitting fiber and overlying tissue is achieved with the detector probe coupled to the photodetector and circuitry of the ECU. The detector probe is maneuvered until an audible sound is broadcast from the ECU, indicating detection of the emitted light from the emitting fiber. Visual detection of the emitting segment of the emitting fiber and overlying tissues is also accomplished with the video camera system.

More specifically, to facilitate infrared transillumination of breast tissue, the emitting end of the fiberoptic light guide is placed in the lumen of the hook wire catheter and the other end is coupled to the near infrared red laser diode of the ECU. Near infrared laser light (810 nm), not visible to the eye, can be detected with a video system that is sensitive to visible and near infrared light. The infrared laser diode can be modulated and detected by the video camera (visible aspect) such that the breast tissue either appears on the video monitor to be "blinking" or is transilluminated continuously. The surgeon also has the option to use the detector probe coupled to the detection panel of the ECU for audible detection of the infrared transilluminated breast tissue (audible aspect). The detector probe is maneuvered until an audible sound is broadcast from the ECU, which indicates detection of the infrared transilluminated breast tissue. The detector probe or the video system can be used by the surgeon to preoperatively or intraoperatively plan their surgical approach or assess their progress intraoperatively.

When using red laser light channel from the ECU, which is visible to the eye, a video camera or the detector probe is not necessary. However, the sensitivity of the video camera and detector probe is greater than the human eye. Furthermore, the transmissivity of near infrared light to visible light in tissue is greater when compared to the transmissivity of red light. As the dissection nears the catheter, the surgeon can switch the emitting fiber from the infrared laser diode channel to the red laser diode channel. Thus, the procedure can continue with the unaided eye.

Over the Wire Catheter

Referring to FIG. 2, an over the wire catheter is transparent and provides a conduit for the delivery of devices such as an emitting fiber or radiopaque stylet (FIG. 2(a)) as well as medicaments or drugs in solution (FIG. 2(c)). The top lumen (FIGS. 2(a) and 2(c)) serves as a guide when the proximal end of a wire previously placed under radiographic guide is placed into the distal entrance of the top lumen and the catheter advanced over the wire to a desired position. The distal end of the lower lumen in FIG. 2(a) is closed. An emitting fiber, radiopaque stylet, or other device can be fitted into the proximal entrance of the lower lumen and advanced to the desired position. FIG. 2(c) shows a side view of the over the wire catheter with the holes in the lower lumen. The distal end of the lower lumen in FIG. 2(c) can be open or closed. In FIG. 2(c), it is shown closed with holes placed in the distal aspect of the catheter. In FIG. 2(c), the lower lumen provides a conduit for the delivery of drug solutions such as anesthetic solutions to a desired site in the breast. In addition, the lower lumen in FIG. 2(c) can also house an emitting fiber, radiopaque stylet, or other device.

Figure 6:
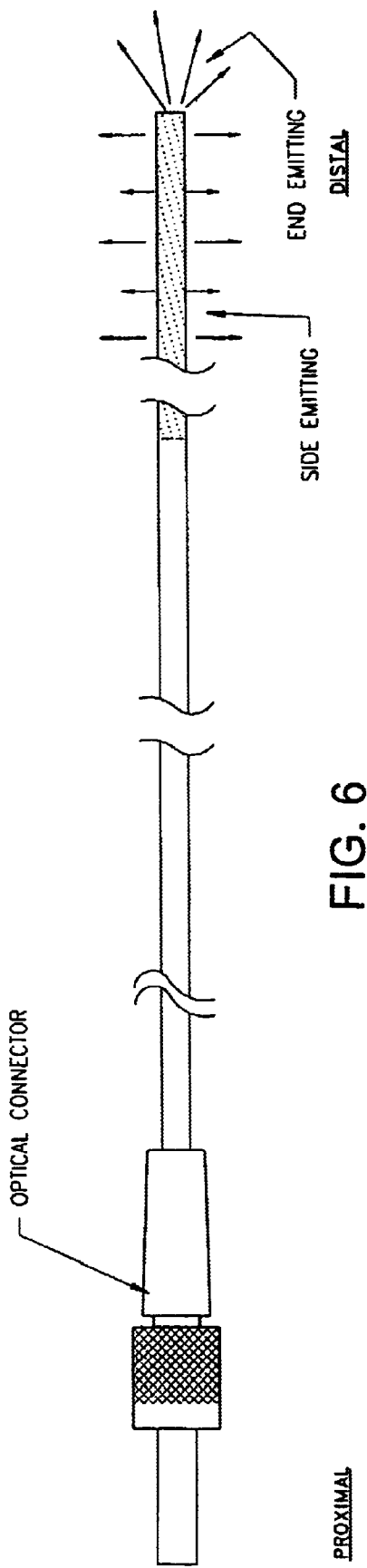
FIG. 6 Side view of a fiberoptic light guide that is end and side emitting.

In the over the wire method (FIGS. 17 and 18), a wire is placed proximate to a breast lesion under radiographic guidance. The proximal end of the wire is fitted into the distal entrance of the wire lumen. The over the wire catheter is advanced to the distal end of the wire or to a desired position. The surgeon can place an emitting fiber (FIGS. 5 and 6), radiopaque stylet (FIG. 4), or other device in the emitting fiber lumen. In addition, the surgeon can also deliver a medicament or drug solution such as anesthetic (FIG. 12; not shown as an over the wire method).

Balloon Breast Catheter

Figure 17:
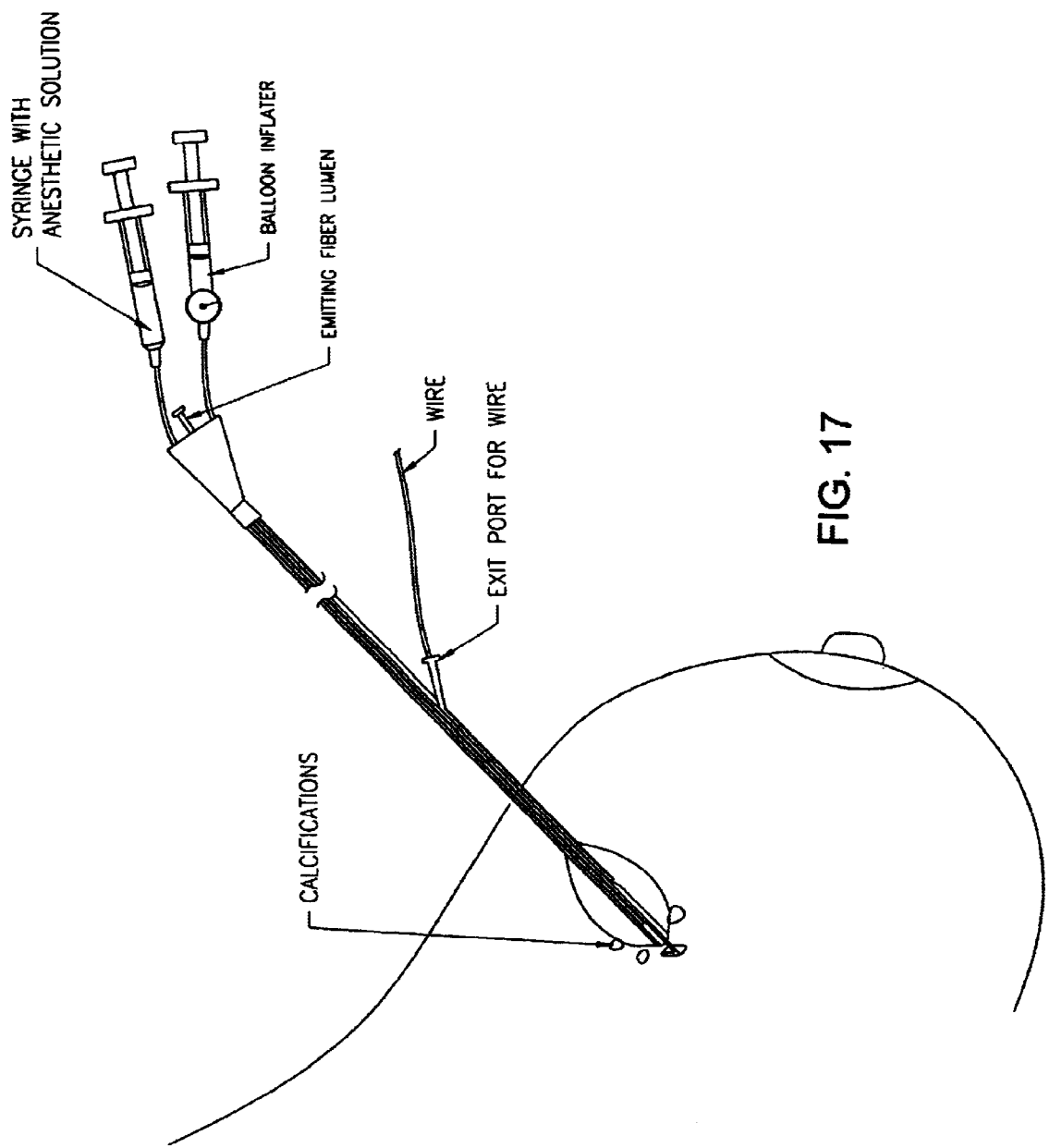
FIG. 17 Schematic of the over the wire emitting fiber drug delivery balloon catheter placed proximate to a breast lesion.
Figure 18:
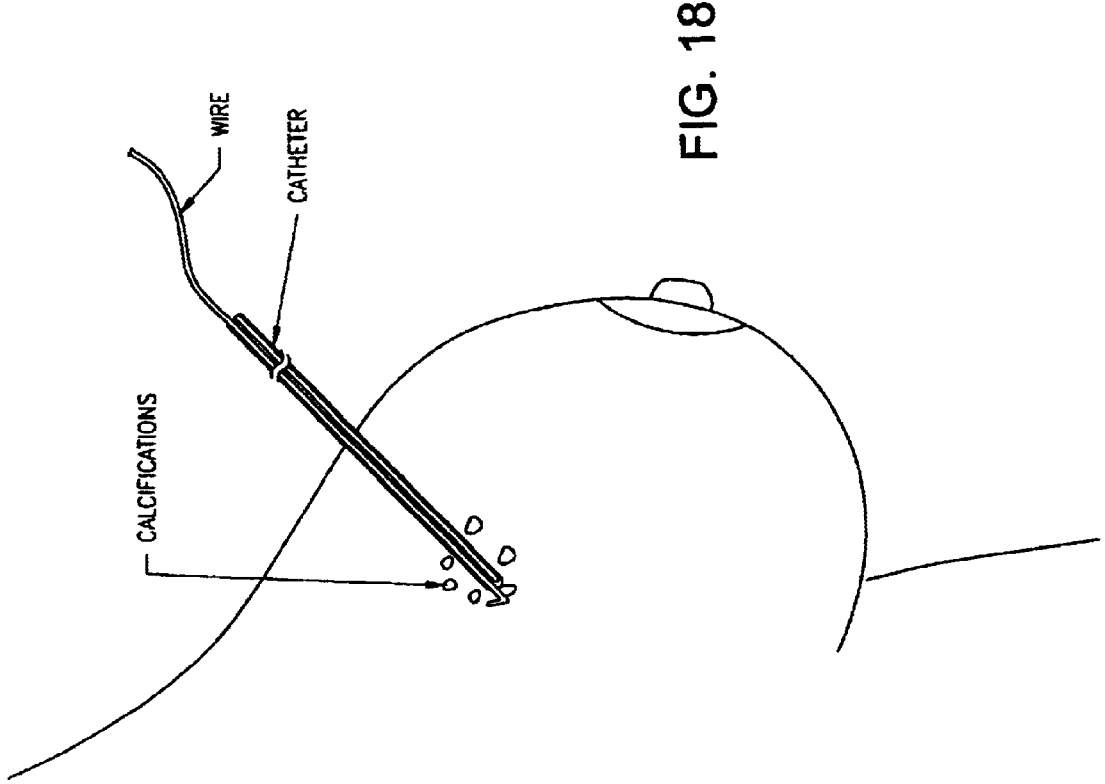
FIG. 18 Schematic of the over the wire catheter placed proximate to a breast lesion.

Referring to FIGS. 13 through 17, an inflated balloon can be used to anchor the catheter in breast tissue. Direct placement of the balloon catheter or an over the wire placement are two methods that be invoked to place the balloon proximate to a breast lesion. For direct placement, the balloon catheter can be reversibly placed in the lumen of a needle (FIG. 7 shows a hook wire catheter, however, a balloon catheter can be placed in the lumen of a needle). The distal aspect of the balloon catheter is introduced into the lumen of needle from the proximal aspect of the needle and advanced as shown in FIG. 7. Once the needle-balloon catheter assembly is placed in the desired position in the breast, the balloon catheter is advanced and emerges from the distal end of the needle. The balloon is inflated using the inflater (FIG. 17). Fluid is discharged from the inflater and enter the lumen of the balloon via the balloon inflation lumen. Inflation of the balloon provides a reversible means to anchor or fix the balloon catheter to a position in the breast. The balloon catheter shown in FIG. 17 is fabricated with multiple lumens including (1) a wire lumen for the over the wire method; (2) a lumen for the reversible placement of an emitting fiber, radiopaque stylet, or other device; (3) a lumen for the delivery of medicament or drug solutions to site in breast tissue along the length of the catheter; and (4) a balloon inflater lumen that transports fluid from the balloon inflater to the lumen of the balloon.

In the over the wire method with a balloon (FIG. 17), a wire is placed proximate to a breast lesion under radiographic guidance. The proximal end of the wire is fitted into the distal entrance of the wire lumen (FIG. 16(a)). The over the wire balloon catheter is advanced to the distal end of the wire or to a desired position. The balloon is inflated thus reversibly fixing the balloon catheter within the breast. The surgeon can place an emitting fiber, radiopaque stylet, or other device in the emitting fiber lumen. In addition, the surgeon can also deliver a medicament or drug solution such as anesthetic (FIG. 12; not shown as an over the wire method).

Inflating the balloon of the balloon catheter allows to surgeon to palpate the balloon or use ultrasound to detect the inflated balloon. In addition, the balloon can be deflated by retracting the plunger on the inflater and removing the balloon from the breast, or repositioning the balloon within the breast and re-inflating the balloon.

In another embodiment, the single lumen catheter in FIG. 1(*a*) that is fitted into the needle in FIG. 4 is replaced with the perforated single lumen catheter shown in FIG. 1(*b*). The perforated single lumen, transparent catheter has holes placed in a staggered fashion along the distal portion of the catheter and function to allow local anesthetic solution such as 2% xylocaine to be delivered along the length of the catheter residing in the breast tissue. The perforated catheter allows improved pain control, anesthesia, and hemostasis at and adjacent to the surgical site. The method used to place the perforated catheter shown in FIG. 1(*b*) is the same as described above for the catheter shown in FIG. 1(*a*). Once the perforated catheter has been placed proximate to the breast lesion, the patient is transferred to the operating room and placed on the operating table. A syringe containing the desired local anesthetic solution is reversibly coupled to the perforated catheter. The desired amount of anesthesia is delivered to the breast tissues lying adjacent to the catheter. With improved pain control and hemostasis, the open surgical biopsy can proceed quicker.

What is claimed is:

1. A method for accessing a target site in solid tissue, said method comprising:

anchoring a catheter having at least one lumen at the target site, wherein anchoring the catheter further comprises deploying a mechanical anchor on the catheter;

positioning a fiberoptic light guide through said at least one lumen within the catheter so that an emitting portion of the fiberoptic light guide is located near the target site;

passing infrared light through the light guide to permit electronic detection of the infrared light emitted from the emitting portion of the light guide;

electronically detecting the infrared light to determine the position of the light emitting portion of the fiberoptic light guide;

surgically accessing the target site based on the position as determined by the electronic detection;

passing visible light through the light guide to permit visual detection of the emitting portion of the light guide; and further surgically accessing the target site based on the position as determined by the visual detection.

2. A method as in claim 1, wherein the infrared light is at a wavelength in the range from 701 nm to 1100 nm.

3. A method as in claim 2, wherein the visible light is at a wavelength in the range from 600 nm to 700 nm.

4. A method as in claim 1, further comprising delivering a fluid agent to the target site through the lumen.

5. A method as in claim 1, wherein anchoring comprises:

placing a wire in the tissue; and passing the catheter into the tissue over the wire.

6. A method as in claim 1, wherein electronically detecting the infrared light comprises manipulating a detector probe through tissue and monitoring the proximity of the probe to the infrared light.

7. A method as in claim 1, wherein electronically detecting the infrared light comprises video monitoring.

* * * * *